United States Patent [19]
Vaillancouert

[11] Patent Number: 6,126,643
[45] Date of Patent: *Oct. 3, 2000

[54] BLOOD COLLECTING SYRINGE

[76] Inventor: Vincent L. Vaillancouert, 14 Bunyan Dr., Livingston, N.J. 07039

[ * ] Notice: Under 35 U.S.C. 154(b), the term of this patent shall be extended for 161 days.

[21] Appl. No.: 08/811,779

[22] Filed: Mar. 6, 1997

[51] Int. Cl.[7] .................................................. A61M 5/00
[52] U.S. Cl. ........................................ 604/218; 600/576
[58] Field of Search .................................. 604/246, 247, 604/218, 228, 187; 600/573, 576, 578, 579

[56] References Cited

U.S. PATENT DOCUMENTS

| | | | |
|---|---|---|---|
| 4,372,325 | 2/1983 | Raitto | 600/576 |
| 5,429,610 | 7/1995 | Vaillancourt | 604/191 |
| 5,522,804 | 6/1996 | Lynn | 604/218 X |

*Primary Examiner*—Danton D. DeMille
*Assistant Examiner*—Justine R. Yu
*Attorney, Agent, or Firm*—McAulay Nissen Goldberg Kiel & Hand, LLP

[57] ABSTRACT

The blood collecting syringe is constructed for coupling with an arterial blood sampling system. In one embodiment, upon retraction of a plunger, a collapsed hollow deformable stopper expands to draw any air bubble and fluid into a small discard chamber within the stopper. Continued retraction of the plunger causes the stopper to also retract thereby forming a specimen collecting chamber within the distal end of the barrel for receiving whole blood from the sampling system. In another embodiment, the plunger has a cap mounted within a hollow stopper so that upon movement of the cap from a forward position within the stopper to a retracted position within the stopper, a discard chamber is formed within the stopper while at the same time, any air bubble and fluid is drawn into the discard chamber. Subsequent movement of the plunger also causes retraction of the nozzle thereby opening up a blood specimen collecting chamber. In each embodiment, an anti-blood clotting agent is disposed between a distal face stopper and the barrel for dissolving in a blood specimen drawn into the specimen collecting chamber.

15 Claims, 3 Drawing Sheets

BLOOD COLLECTING SYRINGE

This invention relates to a blood collecting syringe. More particularly, this invention relates to a blood collecting syringe for collecting blood from an artery. Still more particularly, this invention relates to a syringe for use with an arterial blood gas sampling system.

As is known, various types of arterial blood gas sampling systems have been known for drawing blood from a patient, for example for pressure monitoring and blood sampling purposes. In some cases, these systems employ lines and valves or stopcocks for obtaining a blood flow from a patient with one or more access points at which a syringe may be introduced to obtain a blood sample.

One of the problems encountered in the collection of blood in such sampling systems is the need to eliminate air from the blood sample in order to have a pure sample of blood for analysis. However, even in the most sophisticated systems known, there is a small amount of air, such as 0.2 cc, present which has not been eliminated. To address this problem, use has been made of multiple syringes whereby a first syringe is used to obtain a first fluid discard with an air bubble from the system followed by the use of a second syringe to draw a whole blood sample from the system.

It has also been important for arterial blood gas sampling systems to heparinize the blood sample to prevent premature clotting prior to analysis.

It is an object of the invention to provide an improved syringe for blood collecting purposes.

It is another object of the invention to simplify the taking of a pure blood sample from an arterial blood gas sampling system.

It is another object of the invention to be able to eliminate an air bubble in a blood collecting system in a relatively simple manner.

Briefly, the invention provides a single syringe having a discard chamber for receiving any air and an initial fluid discard from a blood sampling system as well as a specimen collecting chamber for receiving whole blood for sampling purposes.

In one embodiment, the blood collecting syringe includes a cylindrical barrel having a duct at a distal end and a hollow deformable stopper defining a discard chamber therein and being slidably mounted in the barrel to move between a first position adjacent the distal end of the barrel and a retracted position spaced therefrom to define a specimen collecting chamber therebetween. In addition, the syringe includes a valve in a distal end of the stopper to permit a flow of fluid into the stopper as well as a plunger which is slidably mounted in the barrel and connected to the stopper. This plunger is movable between a first position compressing the stopper into a longitudinally collapsed state and a second position remote from the distal end of the barrel to move the stopper into the retracted position thereof. Thus, upon movement of the plunger from the first position toward the second position thereof the stopper first expands from the collapsed state so that fluid from the blood sampling system is drawn into the discard chamber in the stopper along with any air upstream of the valve. The stopper then begins to move from the first position thereof so that fluid from the blood sampling system is drawn into the specimen collecting chamber.

In terms of an arterial blood gas sampling system, in which blood is taken from pressure monitoring lines, an air bubble is normally present which is no larger than 0.2 cc and is due primarily to the dead space within the components of the sampling system, such as a stopcock. To this end, the discard chamber in the hollow stopper may be very small.

In order to satisfy the need of preventing premature clotting of the blood specimen in the specimen collecting chamber, an anti-blood clotting agent, such as heparin, is disposed between a distal face of the stopper and the barrel for dissolving in the blood specimen drawn into the specimen collecting chamber. This anti-blood clotting agent may be retained between the stopper and the syringe in a sealed manner so as to reduce the risk of contamination prior to use. For example, the face of the stopper may have a recess receiving the agent so that when the stopper is abutted against the barrel, the agent is maintained in a sealed relation to a flow of fluid into the barrel until after movement of the stopper from the collapsed state into the retracted position.

In order to maintain the stopper in the collapsed state prior to use, a means is provided for releasably locking the plunger in the first position thereof. Thus, when the syringe is to be used, the locking means is actuated so as to release the plunger thereby permitting the collapsed stopper to elongate into the un-collapsed state. During this time, an initial flow of fluid from the blood collecting system is drawn into the discard chamber along with any air bubble. Thereafter, the plunger is retracted manually so as to draw blood into the specimen collecting chamber. During this time, the stopper moves with plunger into a retracted position.

In another embodiment, the hollow deformable stopper may be formed of two sections with a forward non-collapsible section defining a narrow passageway and collapsible rear bellows-like section defining the main part of the discard chamber. In this embodiment, when the collapsible rear section is expanded, the amount of increased volume therein is sufficient to effect a vacuum within the narrow passageway of the forward section so as to draw in a bubble of air into the discard chamber. This embodiment otherwise functions in a similar fashion as above so that upon further retraction of the plunger, the stopper moves to a retracted position thereby drawing whole blood into a blood specimen chamber between the stopper and the distal end of the syringe barrel.

In still another embodiment, the blood collecting syringe is constructed with a cylindrical barrel, as above, and a hollow stopper which is not collapsible into a collapsed state. In this embodiment, the hollow stopper defines a discard chamber and is slidably mounted in the barrel to move between a first position adjacent the distal end of the barrel and a retracted position to define a specimen collecting chamber with the barrel. In addition, a valve is provided in a distal end of the stopper to permit a flow of fluid into the stopper as well as a plunger which is slidably mounted in the barrel and which has a cap at a distal end slidably mounted within the stopper. The plunger is movable between a first position with the cap disposed in a forward position within the stopper and a second position with the cap disposed in a retracted position within the stopper in order to define a discard chamber within the stopper and to draw a flow of fluid from a blood sampling system into the discard chamber. In addition, the plunger is further movable between this second position and a third position to move the stopper from the first position thereof to the retracted position thereof in order to draw a further flow of fluid from the sampling system into the specimen collecting chamber.

As above, an anti-blood clotting agent is disposed between a distal face of the stopper and the barrel for dissolving in a blood specimen drawn into the specimen collecting chamber.

In use, the cap of the plunger is initially disposed in the forward position within the stopper. After the syringe has been connected to a blood sampling system, the plunger is initially retracted in order to move the cap into the retracted position of the cap within the stopper thereby defining the discard chamber. At the same time, any air bubble and fluid in the sampling system is drawn through the valve at the distal end of the stopper into the discard chamber. After the cap has achieved the retracted position within the stopper, any further retraction of the plunger causes the stopper to move along with the plunger thereby opening up the specimen collecting chamber to a subsequent flow of blood from the sampling system.

In still another embodiment, the syringe may be constructed in a manner such as described in U.S. Pat. No. 5,429,610. In this respect, the syringe has a cylindrical barrel with a duct at a distal end, a stopper slidably mounted in the barrel to move between a first position adjacent the distal end and a second position spaced therefrom to define a specimen collecting chamber therebetween and a plunger slidably mounted in the barrel to move between a first position adjacent the stopper and a second position spaced therefrom to define a discard chamber therebetween. In addition, as described in U.S. Pat. No. 5,429,610, a passageway is disposed between the stopper and the barrel to define a communicating path between the duct and a point between the stopper and the plunger with the stopper in the first position thereof.

In use, when the plunger is retracted, that is moved away from the stopper, any air bubble and fluid from the blood collecting system passes through the passageway between the stopper and barrel to flow into the discard chamber which is being created between the stopper and plunger. Thereafter, subsequent movement of the plunger causes the stopper to move away from the distal end of the barrel thereby forming the specimen collecting chamber. To this end, a collapsible means connects the stopper and the plunger in order to move the stopper with the plunger after a predetermined movement of the plunger from the stopper and after filling of the discard chamber.

In addition, an anti-blood clotting agent is disposed between a distal face of the stopper and the barrel for dissolving in a blood specimen drawn into the specimen collecting chamber.

These and other objects and advantages of the invention will become more apparent from the following detailed description taking in conjunction with the accompanying drawings wherein.

Figure 1:
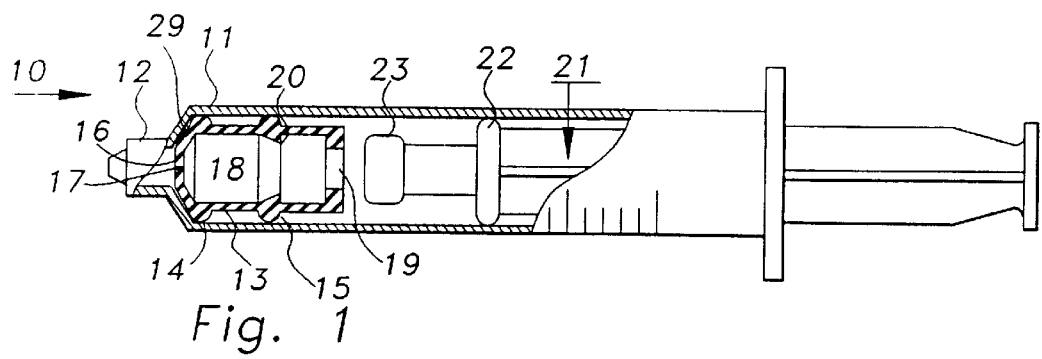
FIG. 1 illustrates a part cross-sectional view of a syringe constructed in accordance with the invention prior to insertion of a plunger into a stopper.

Referring to FIG. 1, the blood collecting syringe 10 includes a cylindrical barrel 11, for example made of any suitable plastic which has an open remote end (not shown) of conventional structure and a duct 12 at a distal end. The duct 12 may be constructed in any conventional manner so as to receive a flow of blood, for example from an arterial blood gas sampling system.

The syringe 10 also includes a hollow deformable stopper 13 which is located at a distal end of the barrel 11. As illustrated, the stopper 13 has a pair of annular ribs 14, 15 for slidably engaging the inside surface of the barrel 11 in a sealed relationship. The annular ribs 14, 15 serve to prevent a flow of fluid from one side of the stopper 13 to the opposite side.

In addition, the stopper 13 has a spherical shaped face 16 for engaging against the distal end of the barrel 11 in a substantially sealed relation. This face 16 may also be provided with small arcuate ribs (not shown) to avoid any frictional lock between the face 16 of the stopper 13 and the barrel 11 when the stopper 13 is to be moved into a retracted position.

The face 16 of the stopper 13 is also provided with a slit 17 which operates as a valve to permit a flow of fluid into and from a discard chamber 18 which is defined within the hollow stopper 13.

The stopper 13 also has an opening 19 at the remote end and an internal annular rib 20 which is spaced from the remote end.

The syringe 10 also has a plunger 21 which is slidably mounted in the barrel 11 in a conventional manner. As illustrated, the plunger 21 has a collar 22 at an intermediate end for guiding of the plunger 21 within the barrel 11. In addition, a cap 23 is formed on the distal end of the plunger 21 for fitting into through the opening 19 in the stopper 13 and serves to mount the stopper 13 on the end of the plunger 21.

Figure 2:
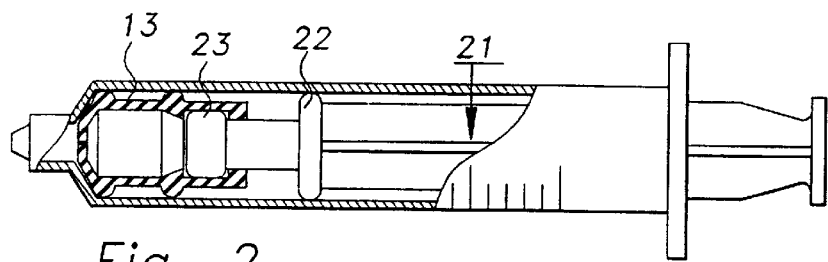
FIG. 2 illustrates a view of the syringe of FIG. 1 with the stopper on the plunger in accordance with the invention.

Referring to FIG. 2, when the cap 23 is inserted into the stopper 13, the cap 23 is held in a friction fit manner between the internal rib 20 of the stopper 13 and the remote end of the stopper 13.

Figure 3:
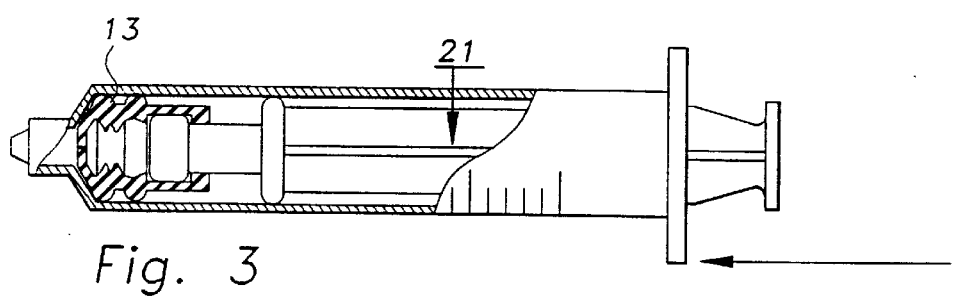
FIG. 3 illustrates a view similar to FIG. 2 with the deformable stopper in a collapsed state relative to the plunger.

After insertion of the stopper 13 and plunger 21 into the barrel 11 (FIG. 1), the plunger 21 is moved into a first position compressing the stopper into a longitudinally collapsed state (FIG. 3). In order to maintain this collapsed state of the stopper 13, the syringe 10 is provided with a means for releasably locking the plunger 21 in this position.

Figure 4:
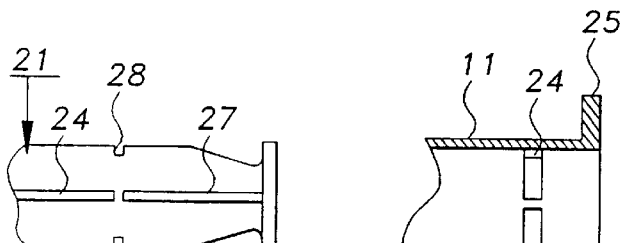
FIG. 4 illustrates a remote end of the plunger of FIG. 1 configured to effect a locking of the plunger in the collapsed state of the stopper in accordance with the invention.
Figure 5:
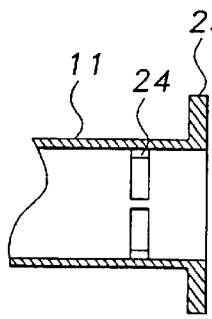
FIG. 5 illustrates a means at the remote end of the cylindrical barrel for releasably locking the plunger in place.
Figure 6:
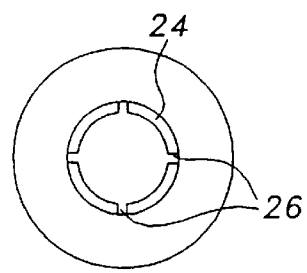
FIG. 6 illustrates an end view of the releasable locking means in the syringe barrel.

Referring to FIGS. 4, 5 and 6, the means for releasably locking the plunger 21 includes a ring 24 formed on an internal surface of the barrel 11 (FIGS. 5 and 6) at the remote end, for example adjacent a conventional flange 25 at the remote end of the barrel 11. As shown in FIG. 6, the ring 24 has a plurality of radially disposed slots 26 corresponding in number to a plurality of longitudinally disposed fins 27 on the plunger 21 (FIG. 4). Each fin 27 is slidably mounted within a slot 26 of the ring 24. In addition, as shown in FIG. 4, each fin 27 is provided with a notch 28 for receiving the ring 24 in response to rotation of the plunger 21 relative to the ring 24 when the notches 28 are aligned with the ring 24. Any other suitable releasable locking means may also be used to secure the plunger 21 relative to the barrel 11.

Referring to FIG. 1, the syringe 10 also includes an anti-blood clotting agent 29, such as heparin, in the form of a pellet, flake, liquid or the like. As indicated, the anti-blood clotting agent 29 is disposed between the distal face 16 of the stopper 13 and the barrel 11 for dissolving in a blood specimen drawn into the specimen collecting chamber which is formed when the stopper 13 is retracted.

In use, after the stopper 13 and plunger 21 combination has been inserted into the barrel 11, the plunger 21 is pushed forwardly so as to collapse the stopper 13 into the collapsed state as shown in FIG. 3 and the plunger 21 is rotated to lock with the ring 24 (FIG. 5). After connection of the syringe 10 to a blood sampling system (not shown), the plunger 21 is rotated to unlock from the ring 24 to allow the plunger to retract under the force created by the expanding stopper 13. That is to say, the stopper 13 tends to expand from the collapsed state as illustrated in FIG. 3 to the expanded state as illustrated in FIG. 2. As such, the plunger 21 is moved into a position remote from the distal end of the barrel. During this time, fluid from the blood sampling system connected to a patient, is drawn along with any air bubble into the discard chamber 18 within the stopper 13 via the valve 17. The volume of the discard 18 is sufficient to receive an air bubble for example of 0.2 cc and some fluid. Thereafter, the plunger 21 is further retracted, manually, so that the stopper 13 is retracted along with the plunger 21 and moves from the position adjacent the distal end of the barrel 11 to a retracted position (not shown) spaced therefrom to define a specimen collecting chamber therebetween, for example, to receive a sample of 2 to 10 cc or more. At the same time, the anti-blood clotting agent 29 is exposed to the blood which is drawn into the specimen collecting chamber.

After the supply of blood to the syringe 10 is terminated, the syringe 10 can be removed from the blood sampling system in a conventional manner so that the blood specimen which is obtained in the specimen collecting chamber can be analyzed. Any air which was in the blood sampling system remains within the discard chamber 18 of the stopper 13 and does not interfere with the blood sampling process.

If the whole blood specimen which has been collected is to be discharged into a receptacle for sampling purposes, the plunger 21 of the syringe 10 is moved forwardly to expel the whole blood sample. During this time, the discard in the discard chamber 18 remains in place in a sealed manner.

Figure 7:
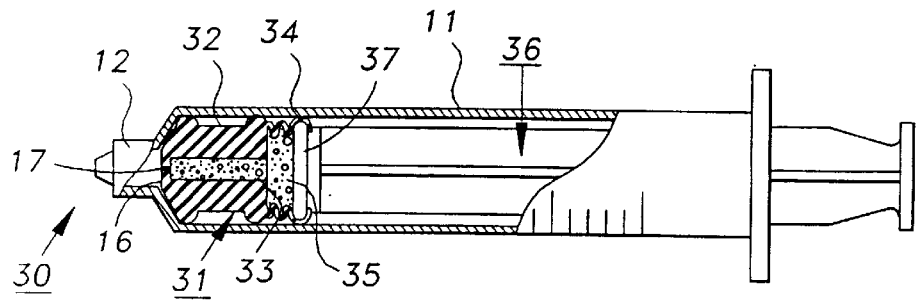
FIG. 7 illustrates a modified embodiment of a deformable stopper employed in accordance with the invention.
Figure 8:
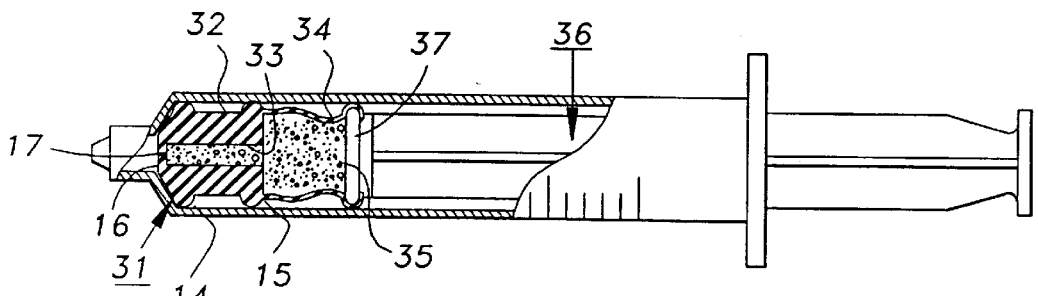
FIG. 8 illustrates a view of the deformable stopper of FIG. 7 in an expanded state within a blood collecting syringe in accordance with the invention.

Referring to FIGS. 7 and 8 wherein like reference characters indicate like parts as above, the blood collecting syringe 30 may be constructed with a cylindrical barrel 11 as above and a modified stopper 31.

In this embodiment, the stopper 31 includes a forward non-collapsible section 32 which defines a narrow passageway 33 and a collapsible rear bellows-like section 34 which defines a main section of a distal chamber 35.

The syringe 30 also has a plunger 36 which is provided with a modified cap 37 which is secured to the remote end of the stopper 31 in a friction fit manner similar to that as described above.

When the syringe 30 is first assembled, the plunger 36 is moved into the position as shown in FIG. 7 so as to collapse only the rear section 34 of the stopper 31. At that time, a releasable locking means as described above with respect to FIGS. 4, 5 and 6 is used to secure the plunger 36 in place. When the syringe 30 is to be used, the plunger 36 is released from the position as shown in FIG. 7 so as to be biased into a retracted position as illustrated in FIG. 8 due to the expansion of the rear section 34 of the plunger 31. During this time, the discard chamber 35 expands thereby creating a vacuum within the narrow passageway 33 which vacuum is sufficient to draw fluid and an air bubble through the slit 17 in the face 16 of the stopper 31 in the manner as described above.

The embodiment of FIGS. 7 and 8 functions in similar fashion to the embodiment of FIGS. 1 to 3. Accordingly, further details of the function of the syringe 30 is not believed to be required.

Figure 9:
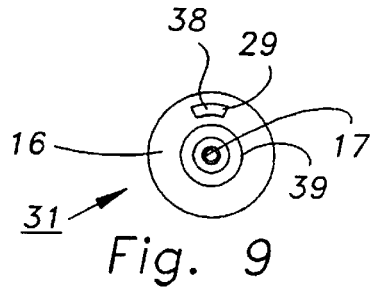
FIG. 9 illustrates an end view of the stopper with a pellet of heparin disposed thereon in accordance with the invention.

Referring to FIG. 9, wherein like reference characters indicate like parts as above, the face of the stopper 31 may be provided with a recess 38 into which the anti-blood clotting agent 29 is positioned in a recessed manner. In this case, the face 16 of the stopper 31 is abutted against the barrel 11 so that the agent 29 is maintained in a sealed relation to a flow of fluid into the barrel 11 until after movement of the stopper 31 away from the distal end of the barrel 11. Alternatively, a ring 39 may be embedded in the face 16 of the stopper 31 circumferentially within the position of the anti-blood clotting agent 29 and about the valve 17 so as to prevent fluid from reaching the agent 29 prior to retraction of the stopper 31.

Figure 10:
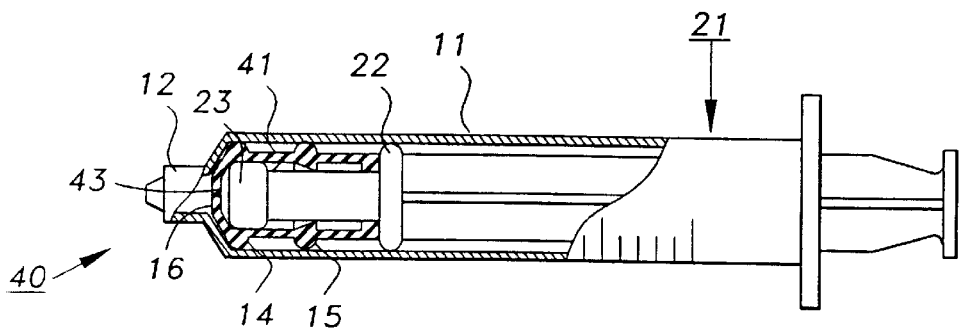
FIG. 10 illustrates a cross-sectional view of a modified blood collecting syringe employing a hollow stopper in accordance with the invention.
Figure 12:
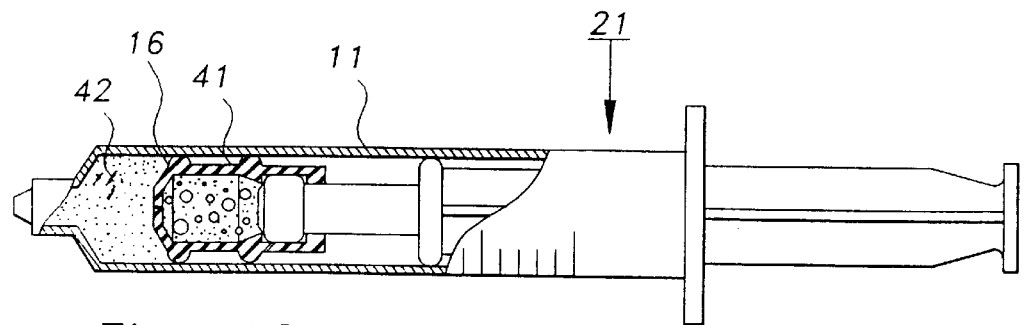
FIG. 12 illustrates a part cross-sectional view of the syringe of FIG. 10 with the plunger withdrawn to define a specimen collecting chamber in accordance with the invention.

Referring to FIG. 10 wherein like reference characters indicate like parts as above, the blood collecting syringe 40 may be constructed in an alternative manner. As illustrated, the syringe 40 includes a hollow stopper 41 which is slidably mounted in the barrel 11 to move between a first position as shown in FIG. 10 adjacent the distal end of the barrel 11 and a retracted position as shown in FIG. 12 spaced from the distal end of the barrel in order to define a specimen collecting chamber 42 therebetween.

As above, the stopper 41 is provided with a pair of annular ribs 14, 15 to seal against the inside wall of the barrel 11.

Figure 11:
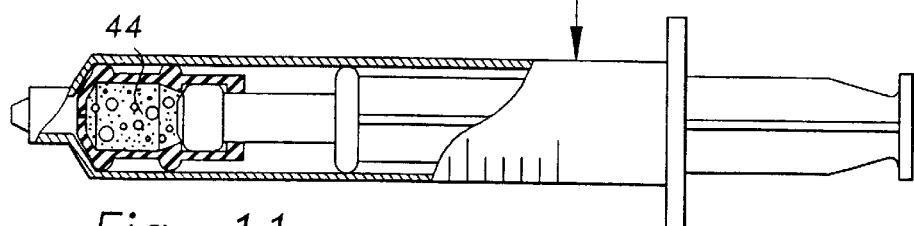
FIG. 11 illustrates a cross-sectional view of the syringe of FIG. 10 with a cap of a plunger retracted within the stopper to define a discard chamber.

The face 16 of the stopper 41 is provided with a valve 43 which permits a flow of fluid into an internal discard chamber 44 (see FIG. 11).

As shown in FIG. 10, the syringe 40 has a plunger 21 similar to that as described above which has a cap 23 which fits into the interior of the stopper 41 to connect the stopper 41 to the plunger 21. However, the plunger 21 has a flange 22 which is spaced a greater distance from the cap 23 so as to permit the cap 23 to be moved into a forward position within the stopper 41 as shown in FIG. 10 and to be retracted into a second position within the stopper 41 as shown in FIG. 11 to define the discard chamber 44 within the stopper 41. During movement of the cap 23 from the forward position of FIG. 10 to the retracted position of FIG. 11, the vacuum which is created within the discard chamber 44 serves to draw a flow of fluid and any air bubble from the blood sampling system into the discard chamber 44. In addition, the internal annular rib 20 of the stopper 41 may be shaped to lock the cap 23 against a return movement in the distal direction, i.e. to the left as viewed.

After the plunger 21 moves the cap 43 into the retracted position shown in FIG. 11, continued retraction of the plunger 21, for example into the position as shown in FIG. 12, causes the stopper 41 to move along with the plunger 21 thereby opening up the specimen collecting chamber 42 between the front face 16 of the stopper 41 and the distal end of the barrel 11. Whole blood is then drawn into the specimen collecting chamber 42.

The whole blood sample which is obtained can then be analyzed in a conventional manner.

Figure 13:
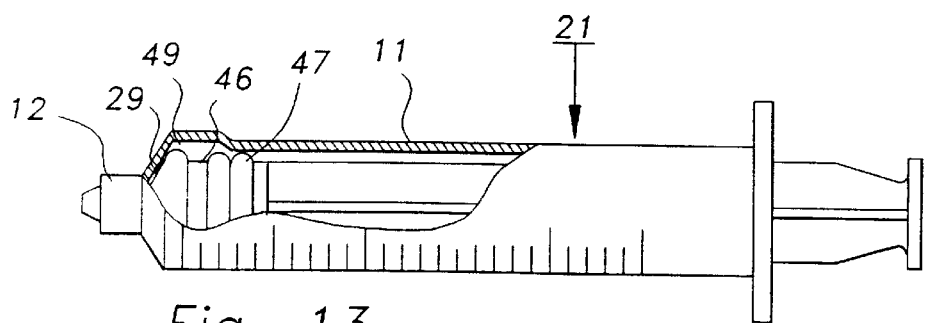
FIG. 13 illustrates a cross-sectional view of a further modified blood collecting syringe constructed in accordance with the invention.
Figure 14:
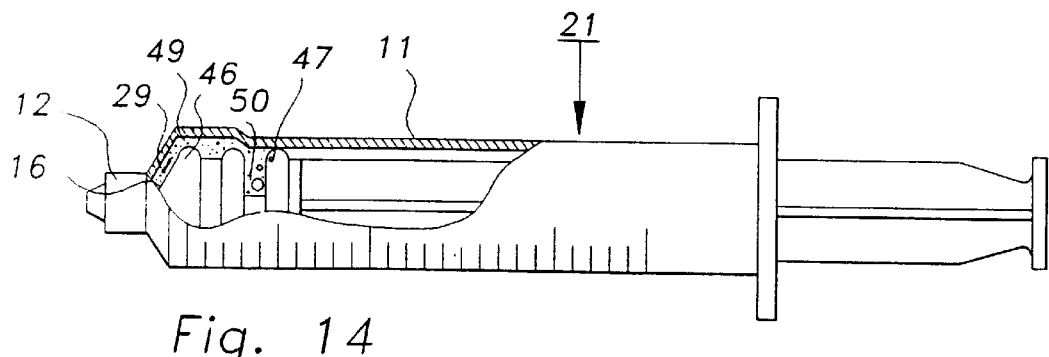
FIG. 14 illustrates a view of the syringe of FIG. 13 in a state defining a discard chamber and a specimen collecting chamber.

Referring to FIGS. 13 and 14, in another embodiment, wherein like reference characters indicate like parts as above, the syringe 45 may be constructed in a manner such as described in U.S. Pat. No. 5,429,610. In this respect, the syringe 45 has a stopper 46 slidably mounted in the barrel 11 to move between a first position as shown in FIG. 13 adjacent the distal end of the barrel 11 to a second position (not shown) spaced therefrom to define a specimen collecting chamber therebetween. The syringe 45 also has a plunger 21 which is slidably mounted in the barrel and which carries a piston 47 at the distal end for sealing against the inside surface of the barrel 11. The piston 47 serves to prevent the flow of fluid from one side of the piston 47 to the opposite side. In addition, as illustrated in FIG. 14, the stopper 46 is connected to the piston 47 by a collapsible means such as a hollow thin wall tube 48, which allows the stopper 46 to move with the plunger 21 after a predetermined movement of the plunger 21 from the stopper 46.

As shown in each of FIGS. 13 and 14, the barrel 11 is provided with a passageway 49 which defines a communicating path between the duct 12 of the barrel 11 and a point between the stopper 46 and the piston 47 of the plunger 21 when the stopper 46 is in the forwardmost position as illustrated in FIG. 13.

In use, when the plunger 21 is first retracted, the collapsible thin wall tube 48 moves from a collapsed position (FIG. 13) to an extended position as shown in FIG. 14. During this time, the piston 47 moves along the inside surface of the barrel 11 thereby creating a discard chamber 50. At the same time, fluid from the duct 12 by-passes the stopper 46 and passes through the passageway 49 into the discard chamber 50 along with any air bubble. Continued movement of the plunger 21 pulls the stopper 46 therealong so that a specimen collecting chamber 51 is formed between the forward end of the stopper 46 and the distal end of the barrel 11 so as to receive a whole blood specimen in a manner as above.

As above, the syringe 45 is provided with an anti-blood clotting agent 29 between the distal face 16 of the stopper 46 and the barrel 11.

The invention thus provides a blood collecting syringe which can be connected to a blood sampling system for collecting a whole blood sample without introducing any air bubbles into the collected specimen.

Further, the invention provides a blood collecting syringe for a blood sampling system which can be used to eliminate air bubbles from the system while also collecting a whole blood sample free of air for sampling purposes.

What is claimed is:

1. A blood collecting syringe comprising
   a cylindrical barrel having a duct at a distal end for connection to a blood sampling system;
   a hollow deformable stopper defining a discard chamber therein and being slidably mounted in said barrel to move between a first position adjacent said distal end and a retracted position spaced therefrom to define a specimen collecting chamber therebetween;
   a valve in a distal end of said stopper to permit a flow of fluid into said stopper; and
   a plunger slidably mounted in said barrel and connected to said stopper, said plunger being movable between a first position compressing said stopper into a longitudinally collapsed state and a second position remote from said distal end of said barrel to move said stopper into said retracted position whereby upon movement of said plunger from said first position toward said second position thereof and expansion of said stopper from said collapsed state, fluid from a blood collecting system connected to a patient is drawn into said discard chamber in said stopper and upon movement of said stopper from said first position thereof fluid from the sampling system is drawn into said specimen collecting chamber.

2. A blood collecting syringe as set forth in claim 1 further comprising an anti-blood clotting agent disposed between a distal face of said stopper and said barrel for dissolving in a blood specimen drawn into said specimen collecting chamber.

3. A blood collecting syringe as set forth in claim 2 wherein said agent is heparin.

4. A blood collecting syringe as set forth in claim 2 wherein said face of said stopper has a recess receiving said agent and abuts said barrel thereat to maintain said agent in sealed relation to a flow of fluid into said barrel until after movement of said stopper from said first position thereof.

5. A blood collecting syringe as set forth in claim 1 further comprising means for releaseably locking said plunger in said first position thereof.

6. A blood collecting syringe as set forth in claim 5 wherein said means comprises a ring on said barrel at a remote end thereof, said ring having at least one slot therein and a longitudinally disposed fin on said plunger slidably mounted in said slot of said ring and a notch in said fin for receiving said ring in response to rotation of said plunger relative to said ring.

7. A blood collecting syringe as set forth in claim 1 which further comprises a valve in a distal end of said stopper to permit drawing of fluid into said discard chamber.

8. A blood collecting syringe as set forth in claim 1 wherein said stopper includes a forward non-collapsible section defining a part of said discard chamber and a collapsible rear bellows like section.

9. A blood collecting syringe comprising
   a cylindrical barrel having a duct at a distal end for connection to a blood collecting system;
   a hollow stopper defining a discard chamber therein and being slidably mounted in said barrel to move between a first position adjacent said distal end and a retracted position spaced therefrom to define a specimen collecting chamber therebetween;
   a valve in a distal end of said stopper to permit a flow of fluid into said stopper; and
   a plunger slidably mounted in said barrel and having a cap at a distal end slidably mounted within said stopper, said plunger being movable between a first position with said cap disposed in a forward position within said stopper and a second position with said cap disposed in a retracted position within said stopper to define a discard chamber within said stopper and to draw a flow of fluid from a blood collecting system connected to a patient into said discard chamber, said plunger being movable between said second position thereof and a third position to move said stopper from said first position thereof to said retracted position thereof to draw a flow of fluid from the sampling system into said specimen collecting chamber.

10. A blood collecting syringe as set forth in claim 9 further comprising an anti-blood clotting agent disposed between a distal face of said stopper and said barrel for dissolving in a blood specimen drawn into said specimen collecting chamber.

11. A blood collecting syringe as set forth in claim 10 wherein said agent is heparin.

12. A blood collecting syringe as set forth in claim 10 wherein said face of said stopper has a recess receiving said agent and abuts said barrel thereat to maintain said agent in sealed relation to a flow of fluid into said barrel until after movement of said stopper from said first position thereof.

13. A blood collecting syringe as set forth in claim 9 further comprising means for releaseably locking said plunger in said first position thereof.

14. A blood collecting syringe as set forth in claim 13 wherein said means comprises a ring on said barrel at a remote end thereof, said ring having at least one slot therein and a longitudinally disposed fin on said plunger slidably mounted in said slot of said ring and a notch in said fin for receiving said ring in response to rotation of said plunger relative to said ring.

15. A blood collecting syringe as set forth in claim 9 which further comprises a one-way valve in a distal end of said stopper to permit drawing of fluid into said discard chamber and to prevent flow out of said discard chamber.

* * * * *

UNITED STATES PATENT AND TRADEMARK OFFICE
CERTIFICATE OF CORRECTION

PATENT NO. : 6,126,643
DATED : October 3, 2000
INVENTOR(S) : Vincent L. Vaillancourt It is certified that error appears in the above-indentified patent and that said Letters Patent is hereby corrected as shown below:

In the Title page change "VAILLANCOUERT" to -VAILLANCOURT-
In Box 76 change "Vaillancouert" to -Vaillancourt- Signed and Sealed this Tenth Day of April, 2001

Attest:

NICHOLAS P. GODICI

*Attesting Officer*   *Acting Director of the United States Patent and Trademark Office*